United States Patent
Karlsson

(10) Patent No.: US 9,983,199 B2
(45) Date of Patent: *May 29, 2018

(54) ARRANGEMENT FOR DETECTION OF HEMOLYSIS

(71) Applicant: HEMCHECK SWEDEN AKTIEBOLAG, Karlstad (SE)

(72) Inventor: Mathias Karlsson, Karlstad (SE)

(73) Assignee: Hemcheck Sweden Aktiebolag (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/363,368

(22) PCT Filed: Dec. 7, 2012

(86) PCT No.: PCT/SE2012/051359
§ 371 (c)(1),
(2) Date: Jun. 6, 2014

(87) PCT Pub. No.: WO2013/085462
PCT Pub. Date: Jun. 13, 2013

(65) Prior Publication Data
US 2014/0329268 A1    Nov. 6, 2014

Related U.S. Application Data

(60) Provisional application No. 61/568,809, filed on Dec. 9, 2011.

(30) Foreign Application Priority Data

Dec. 9, 2011    (SE) ..................... 1151178

(51) Int. Cl.
*A61M 1/00* (2006.01)
*G01N 33/49* (2006.01)
*G01N 33/50* (2006.01)

(52) U.S. Cl.
CPC ....... *G01N 33/5091* (2013.01); *G01N 33/491* (2013.01); *G01N 2333/46* (2013.01)

(58) Field of Classification Search
CPC ............. G01N 33/5091; G01N 33/491; G01N 2333/46
See application file for complete search history.

(56) References Cited

U.S. PATENT DOCUMENTS 4,753,776 A    6/1988    Hillman et al.
5,030,341 A *  7/1991    McEwen ............. B01L 3/50215
                                                    210/515

(Continued)

FOREIGN PATENT DOCUMENTS

EP    0552014 A1    7/1993
GB    1283273 A     7/1972
WO    WO 9623223 A1    8/1996

OTHER PUBLICATIONS

International Search Report from PCT/SE2012/051359, dated Mar. 15, 2013.

(Continued)

*Primary Examiner* — Robert Eom
(74) *Attorney, Agent, or Firm* — Eric L. Sophir; Dentons US LLP

(57) ABSTRACT

The following invention relates to a device for visual detection of hemolysis in a whole blood sample from a pierceable container, said device comprising at least one visible detection compartment and a transfer passage connected to said visible detection compartment, said device further comprising means for passing through the container to the interior of said container for accessing the whole blood and permitting transfer of a volume of plasma from said sample to said detection compartment via said transfer passage, wherein said device further is arranged with a separation device for separating plasma from blood cells (Continued)

within said whole blood sample before said plasma reaches the detection compartment, said device further being arranged with means providing a capillary action for generating a capillary force urging said volume of plasma to be transferred through the separation device to said detection compartment.

8 Claims, 6 Drawing Sheets

(56) References Cited

U.S. PATENT DOCUMENTS

| | | | |
|---|---|---|---|
| 5,133,362 A * | 7/1992 | Moss | A61B 5/1438 600/576 |
| 5,296,192 A | 3/1994 | Carroll et al. | |
| 6,162,639 A | 12/2000 | Douglas | |
| 6,659,975 B2 | 12/2003 | Amano et al. | |
| 8,846,333 B2 * | 9/2014 | Karlsson | A61B 5/15003 435/2 |
| 2001/0044615 A1 | 11/2001 | Amano et al. | |
| 2004/0129678 A1 | 7/2004 | Crowley et al. | |
| 2007/0284298 A1 * | 12/2007 | Samsoondar | A61B 5/14546 210/321.62 |
| 2009/0269799 A1 * | 10/2009 | Winkelman | G01N 1/2813 435/29 |

OTHER PUBLICATIONS

Office Action dated Mar. 19, 2015 corresponding to Chinese Patent Application No. 201280060519.8, 8 pages.
English Translation of Office Action dated Mar. 19, 2015 corresponding to Chinese Patent Application No. 201280060519.8, 11 pages.
Supplementary European Search Report dated Jun. 17, 2015 corresponding to European Patent Application No. 12856331.9, 5 pages.

* cited by examiner

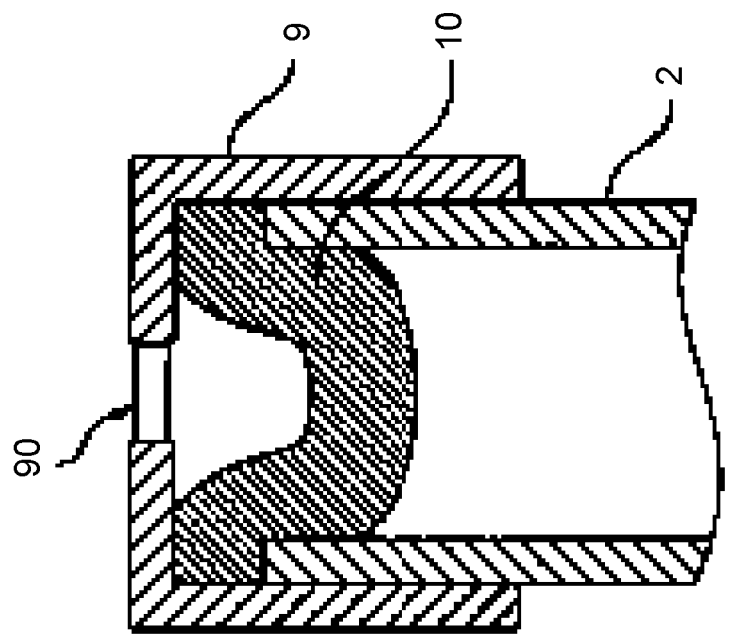
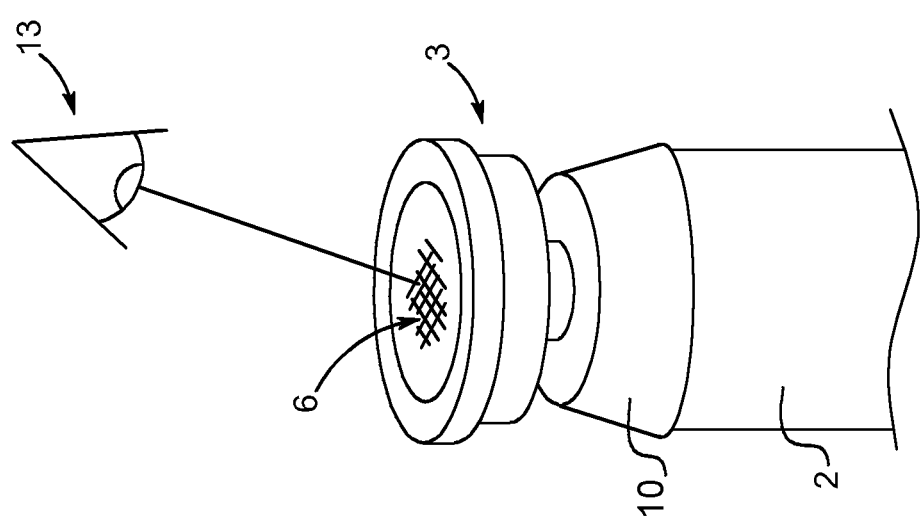
Fig. 3
Fig. 2C

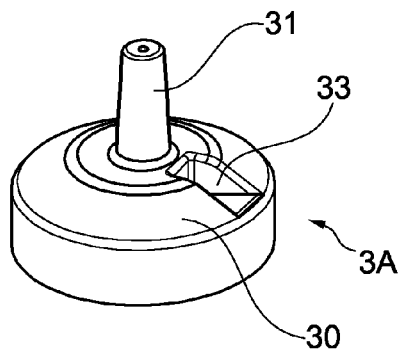
Fig. 4A
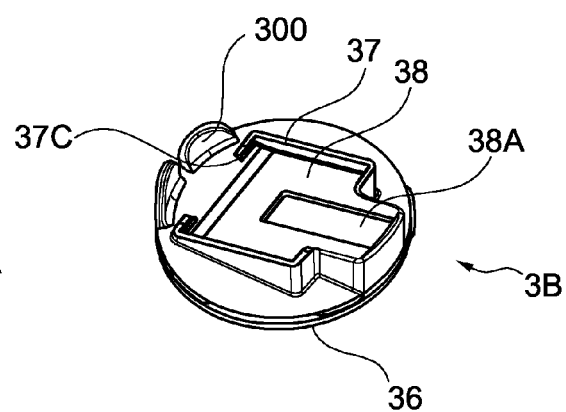
Fig. 4B
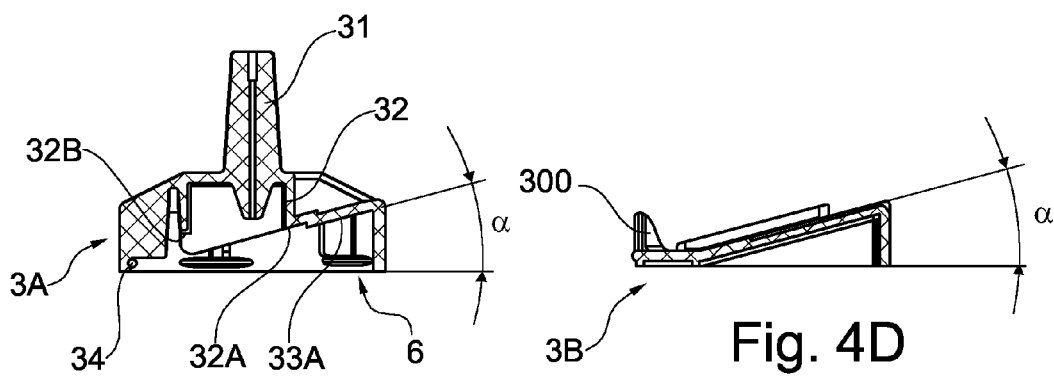
Fig. 4C
Fig. 4D
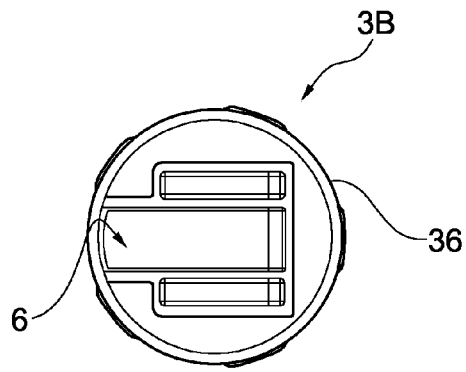
Fig. 4E

ARRANGEMENT FOR DETECTION OF HEMOLYSIS

CROSS-REFERENCE TO RELATED APPLICATIONS

This application claims priority to PCT/SE2012/051359, filed Dec. 7, 2012, entitled "ARRANGEMENT FOR DETECTION OF HEMOLYSIS," which claims priority to Swedish Patent Application No. 1151178-9, filed Dec. 9, 2011, and U.S. Provisional Patent Application No. 61/568,809, filed Dec. 9, 2011, all of which are incorporated by reference in their entirety.

TECHNICAL FIELD

The following invention relates to a device for visual detection of hemolysis in a whole blood sample.

BACKGROUND ART

Laboratory testing is probably the most common clinical routine performed in modern medical care. Cerebral spinal fluid and urine may be used for biochemical analysis, however blood is the body fluid mostly used and these tests are highly important diagnostic and prognostic tools in the everyday patient care.

Laboratory testing could be divided into three phases.
The pre analytic phase: all steps before the actual analysis of a sample including patient variables, collection, handling and processing
The analytic phase
The post analytic phase: test reporting variables Obviously it is of great importance that all three phases are performed correctly since errors could give misleading information to the physicians and therefore jeopardize the well-being of individuals or groups of patients. A majority of the errors seen in laboratory testing occurs in the pre analytic phase, and hemolysis is one of the most significant causes for rejection of specimen. Hemolysis is typically understood as the release of hemoglobin and other intracellular components from erythrocytes to the surrounding plasma, following damage or disruption of the cell membrane. Hemolysis may occur either in vivo or in vitro, and is a most undesirable condition that influences the accuracy and reliability of laboratory testing. Reasons to why hemolysis interferes with multiple biochemical analysis may be e.g. that hemoglobin interferes with the measurements (e.g. spectrophotometric methods), and also that the release of biochemical markers from the broken red blood cells causes false high values of these substances.

Visible hemolysis, as a hallmark of a more generalized process of blood cell damage, is usually not apparent until the separation of serum or plasma has occurred. It is commonly defined as an extracellular hemoglobin concentration of above 0.3 g/L (0.0186 mmol/L), resulting in a detectable pink-to-red hue of serum or plasma.

Generally a collected blood sample needs to be transferred to a distant department where red blood cells are separated from the plasma or serum, for instance by means of centrifugation, and said hue may be detected and reported to the staff in charge of the patient.

Modern laboratories also objectively assess the degree of hemolysis in every blood sample coming in for analysis. If the hemolysis is substantial enough to cause clinically relevant interference to the analysis the result is not reported and a new samples has to be collected from the patient.

Obviously the above described procedures for assessing the validity of the specimen is related to a time delay causing an undesirable situation for the patient as well as leading to circuitous routines.

Alternative detection methods have been suggested, for instance in WO96/23223 which describes a method and apparatus for detecting hemolysis from a blood sample which may be used in a non-laboratory environment. However the detection procedure according to WO96/23223 requires a series of time consuming and inefficient steps leading to a laborious procedure and undesired interruptions.

OBJECTS OF THE INVENTION

It is an object of the invention to provide an improved way of assessing hemolysis in immediate connection to collecting a blood sample, said assessment being possible to perform by a user e.g. in a treatment room without the necessity of a laboratory.

It is a further object of the present invention to provide a rapid way of detecting hemolysis in a whole blood sample, wherein an assessment preferably can be made within one minute, preferably within less than 30 seconds from initiating use of a device according to the invention.

It is a further object of the invention to provide a way of assessing hemolysis with only a very small volume of whole blood sample, preferably between 2-100 µl whole blood, preferably resulting in between 1-50 µl plasma volume for detection.

It is a further object of the present invention to provide a way of assessing hemolysis which is intuitive and easy to handle, preferably wherein the person collecting a blood sample may perform the steps for detecting hemolysis by using one hand only.

These and still other objects of the invention will become apparent upon study of the accompanying drawings and description of the invention.

SUMMARY OF THE INVENTION

The objects of the invention are achieved by means of a device for visual detection of hemolysis in a whole blood sample from a pierceable container, said device comprising a dispensing body including a surface arranged to engage with the stoppered container, at least one visible detection compartment and a transfer passage connected to said visible detection compartment, said device further comprising means for passing through the stoppered container to the interior of said stoppered container for accessing the whole blood and permitting transfer of a volume of plasma from said sample to said detection compartment via said transfer passage, wherein said device further is arranged with a separation device for separating plasma from blood cells within said whole blood sample before said plasma reaches the detection compartment, said device further being arranged with means providing a capillary action for generating a capillary force urging said volume of plasma to be transferred through the separation device to said detection compartment.

The device according to the invention allows for a quick and easy way of transferring a whole blood sample from inside a container (such as a stoppered collection tube, a blood bag or any other blood containing container) via said transfer passage to the detection device according to the invention. Providing of said capillary force will lead to the advantage of efficient plasma separation through a separation member (e.g. a filter) and of reliable transfer of the resulting plasma sample into the detection compartment, where no additional external force being necessary for acquiring said transfer.

It is understood that a "user" may refer to any person operating the device for detecting hemolysis and may include e.g. a medical practitioner, a health care provider and/or a laboratory personnel or a veterinarian.

In the following description "blood collection arrangement" shall be understood to include (in a non-limiting sense) a stoppered container, a collection tube, a blood collection tube, a conventional tube a blood bag and a capillary tube. Furthermore, a test tube may refer to a stoppered tube, a collection tube, a blood collection tube, a conventional tube and vice versa.

A "stoppered tube" refers to a, normally airtight, container of glass, plastic or the like, arranged to contain a volume of liquid biological specimen therein, such as a whole blood sample. Normally, such stoppered tubes are provided with an open end having a pierceable stopper or sealing member (of rubber or the like) positioned in the open end. Such construction is typical for closed specimen tubes which are manufactured under reduced atmospheric pressure and that they lose all or most of their vacuum when filled.

According to another aspect of the invention said means providing a capillary action comprises a separation filter and a detection member, wherein the separation filter is arranged to abut an orifice of the transfer passage and the detection member is arranged to abut the separation filter in such a way that the separation filter is sandwiched between the orifice of the transfer passage and the detection member, wherein the detection member further is visibly arranged inside detection compartment (60). Thanks to the separation device (e.g. separation filter) the whole blood is efficiently separated from the plasma which may subsequently become easily analyzed once being visible inside the detection compartment.

As will later be described in more detail, the detection member may be in the form of a detection filter comprising a structure which provides a capillary action or it may equally be in the form of a porous structure which provides a capillary action. Examples of suitable materials may include glass fiber as well as any porous material giving rise to said capillary force which will contribute to transfer of the plasma. The skilled person understands that "capillary action", or "capillarity", may be interpreted as the ability of a liquid to flow against gravity where liquid spontaneously rise in a narrow space such as in porous material like paper or filter. Thus, said detection filter may be made of any suitable material which provides said capillary action and fulfils other requirements of the present invention, such as glass fiber material, a woven filter or a non woven-filter or even certain cloth materials may prove suitable for the purpose.

In a preferred aspect of the invention, said means for passing through the pierceable container comprises a needle element having a first end portion for penetrating the sealing member of a pierceable container and a second end portion arranged at the housing of the device and adjacent to said separation filter. It is to be understood that "adjacent to" here shall be interpreted in a way that the needle element is positioned with its second end portion, and the mouth/orifice at the corresponding second end portion, positioned adjacent to the separation filter so that any whole blood passing through the needle upon exiting the needle will proceed onto the separation filter. Preferably there is a small distance between the needle mouth and the separation filter so that the blood volume may readily spread out onto the filter once applied thereon.

Once a volume of blood is applied onto the separation filter it will get drawn into the structure of the separation filter directly upon exiting said transfer passage (e.g. needle), thanks to capillary action, whereby the plasma is separated from the red blood cells. The adjacently positioned detection filter in its turn is arranged to also provide capillary action meaning that the volume of plasma, upon having passed the separation filter, will continue to get drawn into the detection filter to such an extent that it becomes visible on the opposite side of the detection filter as the plasma is transferred therethrough. The detection filter is in its turn preferably is visibly arranged inside detection compartment (60), and may thereby be readily observed by a user. Since hemolysis is visually detectable in serum or plasma the arrangement according to the invention provides an opportunity for the person collecting a sample to, immediately upon that the plasma becomes visible in the detection compartment by means of having wetted the detection member, visually determine if a clinically significant hemolysis is present in the sample before the tube containing the sample is sent to the laboratory. Such determining of hemolysis may be done by merely observing the hue of the plasma portion which has been absorbed by the visible detection filter inside the detection compartment (i.e. if the plasma is amber no hemolysis has occurred, but if the plasma is light pink to red hemolysis can be suspected and a new blood sample should be collected).

In case of rejected specimen due to occurred hemolysis in the collected blood sample the invention will also enable for, possibly even prior to the sample equipment is removed from the patient, collection of a new sample more suitable for analysis. This leads to many advantages. The situation for the patient will be considerably improved since the risk for required recollection of a blood sample is reduced when using the inventive detection device. The time delay caused by the laboratory hemolysis testing is eliminated leading to quicker processing of blood sample analysis which of course means more rapid delivery of results/diagnosis as well as higher success rate in following sample analysis and cut costs.

Thanks to the device according to the invention there is provided a way of detecting hemolysis in a collected blood sample which comprises very few steps, which is easy and intuitive, which is quick, requires only a small sample volume and which can be performed using one hand only in immediate connection (e.g. bedside) to a patient.

Preferably, the separation filter as well as the detection member (e.g. detection filter) comprise a porous structure generating a capillary action whereby plasma is urged to pass through both of the respective filters. The visual examination of plasma hue is performed the moment plasma has been drawn into the structure detection member to such an extent that the plasma is visible through the transparent cover of the detection compartment. It is to be understood that the detection compartment may contain merely the detection member and that the detection compartment is covered by a transparent cover through which the interior of the detection compartment may be observed. The detection compartment may be provided with the detection member in the form of a detection filter, or it may be filled with another detection member in the form of a porous material such as glass wool which also provides the desired capillary action leading to that separated plasma is sucked up into the structure of the detection member to such extent that the detection member is colored by the hue of the plasma whereby assessment of hemolysis in the blood sample may be determined by looking at the hue of the detection member.

By means of providing filter (i.e. separation filter and detection filter) or porous material in the detection compartment the risk of bubble formation is significantly reduced.

By means of said separation filter and detection member a capillary action is achieved resulting in an efficient plasma transfer. Another advantage provided by means of having one separation filter and one additional detection filter is that the red blood cells will get stuck in the separation filter, meaning only plasma is transferred further through the second filter. In addition to providing an extra capillary action force, the second filter will thus also provide a shielding function, shielding off any red color on the first separation filter from being detectable/visible/perceptible inside the detection compartment. This is an advantage since the detection according to the invention requires safe and reliable determination of plasma hue, and any red color from separated blood cells could risk disabling correct assessment of hemolysis.

Preferably, said detection filter has a color which provides an easy assessment of the plasma hue, e.g. a white filter color, meaning that the detection filter facilitates detection of a color change which indicates occurrence of hemolysis. This means that the detection filter, in addition to the above mentioned advantages, also facilitates the actual detection as it provides a detection surface making it easier to detect hemolysis. The color of the detection filter may be some other color than white in order to further facilitate proper detection of plasma hue. For instance, said detection filter may have a light blue color for intensifying color differences and facilitate correct detection: an amber-colored plasma on light blue filter would result in a final greenish detection color whereas pink-colored plasma on light blue filter would yield a purple detection color.

According to yet another aspect of the invention said means providing a capillary action comprises a separation filter, a detection filter and a separating distribution surface, wherein the separation filter is arranged to abut an orifice of the transfer passage, the separating distributing surface is sandwiched between the separation filter and the detection filter, and wherein the detection filter further defines the bottom portion of said detection compartment. The separation distribution surface provides the advantage of further safeguarding that possible red color on the separation filter resulting from the separated red blood cells will not interfere with the visual assessment of the color of the plasma inside the detection compartment. Further, the separation distribution surface has the function of distributing the plasma from the separation filter before it contacts the detection filter so that the plasma is distributed more evenly into the detection compartment.

According to another aspect of the invention, said detection compartment and said separation device are arranged within a housing, and the means for passing through the stoppered container comprises a needle element having a first end portion for penetrating the sealing member of a stoppered container and a second end portion arranged at the housing and positioned adjacent to said separation filter.

According to another aspect of the invention, the cross sectional filter area of said separation filter is substantially larger than the cross sectional area of said transfer passage in order to eliminate risk for clogging of the filter According to yet another aspect of the invention said separation device is a separation filter (or separation membrane) arranged to separate plasma from the cellular components of whole blood sample without lysis. It is understood that the filter may be any known conventional filter or membrane which meets the separation requirements of the present equipment, including membranes made from synthetic as well as natural polymers, preferably but not necessarily a hydrophilic membrane. According to one embodiment the separation filter is asymmetric meaning the filter pores have varying sizes. The filter may have any suitable geometry or shape, e.g. being substantially flat or being three dimensional, e.g. cylinder shaped. The size and/or volume of the filter depend on the filter type as well as the specific plasma volume that is to be separated there through.

According to yet another aspect of the invention said at least one detection compartment may be arranged with chemical means for direct visual detection of hemoglobin. The chemical means for visual detection may lead to a change of color in case hemolysis has occurred whereby it is permitted for safer and more reliable test results and easier evaluation, especially in case there is only a slight hue of pink where correct assessment by just looking at the color of the plasma might prove to be difficult. The chemical means may be dry chemical means and may for instance be dried into the structure of the detection member (e.g. into the filter).

According to yet another aspect the detection member is a filter made of glass fiber which has a thickness between 0.1-1 mm. According to yet another aspect the detection member is a filter made of a porous material with a thickness between 0.1-5 mm.

BRIEF DESCRIPTION OF THE DRAWINGS

The invention will now be described more in detail with reference to the appended drawings, wherein:

FIG. 3 illustrates schematically the top portion of a conventional collection tube, FIGS. 4A-E shows a third embodiment of a detection device in accordance with the invention.

DETAILED DESCRIPTION OF THE INVENTION

The foregoing aspects and many of the attendant advantages of this invention will become more readily appreciated as the same become better understood by reference to the following detailed description, when taken in conjunction with the accompanying figures. Further, the description, and the examples contained therein, are provided for the purpose of describing and illustrating certain embodiments of the invention only and are not intended to limit the scope of the invention in any way.

Figure 1A:
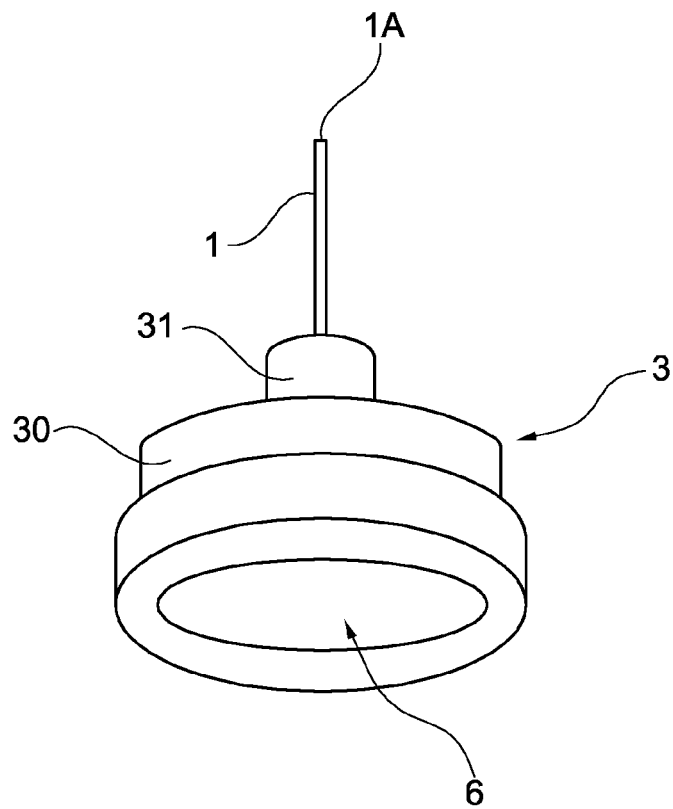
FIG. 1A is a perspective view, schematically showing a preferred embodiment of the device according to the invention.
Figure 1B:
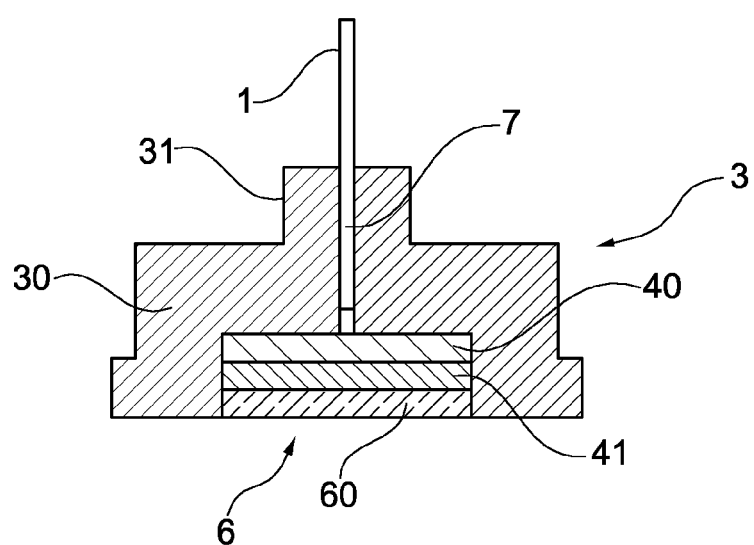
FIG. 1B is a cross-sectional view of the device in FIG. 1A, FIGS. 2A-C illustrate in a schematic way the use of a device according to the invention.

FIGS. 1a-b show a preferred embodiment according to the invention. Herein FIGS. 1a-b schematically illustrate a detection device 3 arranged to visually indicate hemolysis in a blood sample 12, FIG. 1a showing a perspective view of the assembled device 3 and FIG. 1b shows in a simplified and schematic way a cross section of a detection device 3 according to the exemplary embodiment of the invention in FIG. 1*a*.

Figure 2A:
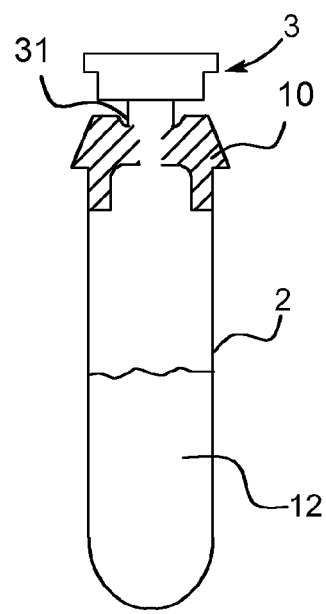
Figure 2B:
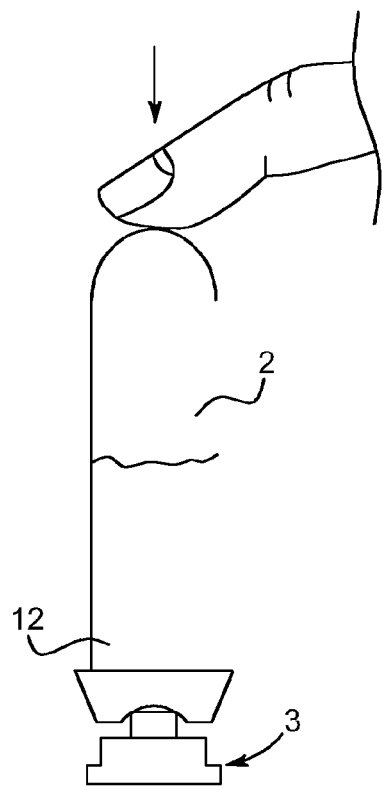

FIGS. 2*a-c* further show the principle for performing a quick instant testing of hemolysis of a blood sample 12 in a collection tube 2, by means of a detection device 3 according to the present invention.

Referring firstly to FIGS. 1*a-b*, in its first end said detection device 3 comprises a means 1 for passing through a stoppered container 2 in the form of a needle element 1 which in non-operational mode is preferably provided with a protecting cover (not shown) e.g. made of rubber. It is to be understood that the device 3 shown e.g. in FIGS. 1*a-b* is not to be seen as limited to the specific dimensions shown therein, and that for instance the needle element 1 may in reality be longer than in the drawings. The needle 1 has a first end part 1A creating a tip for passing through the sealing member of a stoppered container 2 to the interior of said stoppered container 2 for accessing the whole blood 12 therein. The needle 1 further has a second end being arranged inside a housing 30 of the device 3 and abutting a separation device, preferably a separation filter 40. A transfer channel 7 is defined by the pathway/passage between the needle tip 1A and the needle end at the housing 30, providing for passage of blood 12 from the container 2 to a visible detection compartment 6 preferably positioned at the second end of said detection device 3, said second end being opposite to said first end. The needle 1 and the transfer channel 7 together forms a transfer passage 1, 7 for the sample. Subsequent to the needle piercing a stopping member of a container 2 and getting in contact with the specimen 12 therein, said transfer passage 1, 7 is arranged to permit transfer of a volume of plasma from said container 2 to said detection compartment 60 via the separation filter 40 (as will later be described in more detail). The separation filter 40 is thus arranged to be brought into contact with a blood sample 12 and permit passage of free hemoglobin and stop passage of red blood cells thus allowing for the passage of blood plasma 14. The plasma is drawn through the separation filter 40 by means of capillary action which is generated as the plasma contacts the filter body, due to the porous material which constitutes the filter 40. Hereby a volume of blood will get drawn into the structure of the separation filter 40 directly upon exiting said transfer passage 1, 7 (e.g. needle), thanks to capillary action, whereby the plasma is separated from the red blood cells. As seen in FIG. 1*b* (showing one embodiment of the invention), a detection means in the form of a filter 41 is abutting the separation filter 40. The abutting detection filter 41 is arranged to also provide capillary action meaning that the volume of plasma, upon having passed the separation filter 40, will continue to get drawn into also the detection filter 41. The plasma will thereby get transferred into the detection filter 41 to such an extent that the plasma wettens substantially the entire thickness of the filter structure 41 and becomes visible from the other side of the filter 41. As the detection filter 41 also constitutes the bottom portion of the visible detection compartment 6, the plasma may hereby be readily observed by a user.

It is to be understood that the separation filter 40 and the detection member 41 (e.g. filter 41) may be positioned in other ways in relation to each other than shown in FIG. 1*b*. As previously described, in FIG. 1*b* the separation filter 40 and the detection filter 41 are positioned vertically adjacent to each other, and abutting each other, so that plasma will be transferred along a pathway aligned with the longitudinal axis of the needle. In another embodiment it is possible to position the separation filter 40 and the detection filter 41 essentially side-by-side (in a horizontal alignment) inside said housing 30. This means that, like in the previously described embodiment, blood will firstly become applied onto the separation filter 40 from the needle resulting in the separation of red blood cells from the plasma. On the opposite side of the separation filter, or at the side thereof there is arranged a channeling means, which leads the separated plasma to the detection filter 41. In a preferred, the separation filter 40 and the detection filter 41 may partially overlap each other, said detection filter 41 being positioned on one side of the separation filter 40 and thereby also acting as a channeling means. Hence the plasma is transferred through the separation filter 40 to reach the detection filter 41 via said channeling means. As soon as the plasma gets into contact with the detection filter body 41 it will get drawn into the detection filter structure by means of said capillary action. It is foreseen that the channeling means may be in the form of a separate channel between the separation filter 40 and the detection filter 41.

Preferably the surface of the filters 40, 41 which are arranged to contact the blood sample are substantially much larger (e.g. at least ten times) than the cross sectional surface of the needle 1 cross section, in order to eliminate risk for clogging of the filters 40, 41. It is to be understood that the separation filter 40 and the detection filter 41 may have different dimensions (e.g. diameters), for instance the detection filter 41 may have a smaller diameter than the separation filter 40.

Between the separation filter 40 and the detection filter 41 there may be arranged a distribution surface (not shown). The distribution surface is preferably provided with passages (e.g. channels, openings, pores, slits or any other suitable passage type) for allowing passage of plasma from the filter 40 and at the same time leading to a plasma distribution over the adjacent detection filter 41 so that the plasma to be examined is evenly distributed over said filter 41. An even plasma distribution will lead to safer assessment of hemolysis. The distribution surface is preferably arranged to not allowing any passage of color (i.e. red color from filtered blood cells), and may for this reason for instance be formed by a non-transparent material which blocks any light from passing/shining through the body.

The detection compartment 6 is visibly arranged at a bottom portion of the body 30 of the detection device 3. Preferably the detection compartment 6 is covered by some suitable transparent cover material 60 through which a user can readily observe the interior of the detection chamber 6, e.g. for determining when plasma has been sucked up into the detection filter 41 and whether the hereby visible hue of such plasma would indicate that hemolysis has occurred. In one embodiment the side of the detection filter 41 which is intended to face the transparent cover, and which will correspond to the background surface of the detection compartment 6, has a white color for the purpose of facilitating color assessment of plasma (e.g. amber or pink). In one embodiment of the invention said detection compartment consists merely of said detection filter covered/protected by a transparent cover plate 60 at the bottom of the housing 30.

In one embodiment of the invention it is conceivable that the bottom portion of the device 3 (either inside the detection compartment 6 or next to the visible detection well at the outside of the detection device body 30) there is arranged a color reference scale for comparison with plasma hue. Such reference scale could further simplify a correct assessment regarding hemolysis.

Preferably the detection filter 41 has a thickness between 0.1-5 mm. The size diameter of the detection compartment 6 is preferably adapted to convenient visual detection, i.e. adapted so that a user can easily observe the interior of such detection compartment. Preferably the detection device 3 is arranged to filter a volume of between 2-100 μL whole blood resulting in about between 1-50 μL plasma for visual observation.

According to one embodiment said detection filter 41 is arranged with chemical means for direct visual detection, meaning that a reagent/reagents may be deposited onto and dried into the detection filter 41 which reacts with hemoglobin and produces a color for indicating if hemolysis has occurred.

The device 3 may further comprise a transparent hydrophilic tape for facilitating transfer of plasma into the detection compartment 6. For the same reason (i.e. facilitate plasma transfer) the surface of said detection filter 41 may comprise a hydrophilic surface treatment such as coating, surfactant or plasma surface treatment for improving wetting and plasma distribution.

In FIG. 2a-c there is illustrated one exemplary use of a detection device 3 according to one embodiment of the invention. Typically a collection tube 2 as referred to herein is constructed of glass material or plastic such as polypropylene, polystyrene, polyethylene terephtalate or any other suitable polymer. Preferably the collection tube 2 has an elongate shape with a circular wall, having one closed end and one open end defining a chamber therein for receiving sample of a collected fluid (e.g. blood 12) from a patient. The open end is tightly sealed with a resilient sealing member 10 (see FIG. 3). The sealing member 10 (e.g. a sealing plug) can be made of rubber or some other suitable resilient material, and is disposed at the open end of the tube 2 to close the chamber and hermetically seal the interior of the tube. Further, the open end of the 2 may or may not be protected by a protecting lid 9 attached onto tube 2 and over the sealing member 10. If covered by a lid, said lid 9 comprises a central opening 90 intended for passage of a needle 1 arranged to penetrate the sealing member 10. It is understood that the tube 2 illustrated in FIG. 3 shall be seen only schematically and that the particular dimensions e.g. of the central opening 90, shall merely be looked upon as explanatory and for the better understanding for the reader. Thus the dimensions of the tube in FIG. 3 are not to be seen as limiting for the function and/or use of the present invention. Likewise, the tubes shown in FIG. 2a-c are shown without said lid 9, however the skilled person understands that both types (i.e. with or without lid 9) are conceivable for the purpose of functioning of the present invention.

Dispensing of a blood volume 12 from inside the collection tube 2 (stoppered container 2) to the detection device 3 is accomplished by means of a method described in U.S. Pat. No. 5,344,666, which is hereby incorporated by way of reference. The principle for dispensing a blood volume is as follows. As seen in FIG. 2a the device 3 is assembled to the sealing member 10 by pressing the needle tip 1A through the centre of the sealing member 10, for instance but not necessarily when the container is in an upright position. It is also imaginable to press the sealing member 10 onto the needle tip 1A as the device is positioned with the needle pointing vertically upwards, said device 3 resting on a surface. Possibly said device 3 may then be placed inside some supporting holding structure (not shown) safeguarding that it is kept in a rightful position and doesn't fall or move. The latter option enables for a user to use one hand only when performing the method according to the invention. If however the container is (or is positioned into) an upright position when the device 3 is connected thereto any pressure difference which might exist between the inside of the container 2 and the atmosphere is neutralized by means of air being able to pass through the needle 1. The needle 1 is held in a boss like annular abutment member 31 (also referred to as a dispensing body 31) including a surface arranged to engage with the stoppered container 2. The dispensing body 31 limits the length of the needle 1 that can penetrate the rubber sealing member 10. This length is sufficient to penetrate the sealing member 10 and enters an additional distance into the well space which is immediately adjacent to the inner surface of the sealing member in order to get into contact with the liquid sample (whole blood) disposed therein.

The diameter of the annular dispensing body 31 is smaller than the average concave diameter of sealing member concave depression and the dispensing body 31 is also longer than the maximum depth of concave depression of the sealing member 10 so that dispensing body 31 is always operative to effect a flexing or distortion of rubber stopper 10 to force same inwardly of the container.

As previously described the device 3 is very simply connected to a collection tube 2 by forcing the piercing tip 1A of the needle 1 through the central portion of the sealing member 10 until the annular dispensing body 31 reaches the depth of the concave depression of the sealing member 10 (see FIG. 2a) wherein the device 3 is ready for use as seen in FIG. 2b. In FIG. 2b the closed tube container 2 with attached device 3 is shown in the inverted operating position, having been assembled in the manner already described. When container and device 3 is pressed by manual force against a surface, downward force is resisted by the underlying surface (e.g. a bench top). This creates an internal compression force within the sealing member 10 which deforms said sealing member 10, thereby reducing the volume inside the container 2 and ejecting a small amount of liquid (blood 12) through the needle 1 and further onto the previously described filters 40, 41. Said small volume of whole blood 12 will thereby become drawn through the separation device by means of capillary action and plasma is thus transferred to the detection compartment as previously described, whereupon assessment of plasma hue may be performed (illustrated in FIG. 2c).

As shown in FIG. 2c, the user 13 may turn the tube 2 which is still connected to the detection device 3, for visually inspecting the detection compartment 6 and the plasma therein hereby being able to determine whether or not hemolysis has occurred in the blood sample 12: if the plasma is amber no hemolysis has occurred, but if the plasma is pink hemolysis can be suspected and the blood sample 12 should be replaced by a new one. In order to simplify assessment of hemolysis the device may be provided with a color reference for comparison with the sample plasma, e.g. showing a cutoff color wherein if the plasma color is darker than the reference hemolysis can be suspected and vice versa. Such color reference may for instance be arranged next to the visible detection compartment 6 on the top portion of the device 3.

If no hemolysis has occurred the detection device 3 is removed from the tube 2 and discarded as waste material, and the tube 2 with the sample 12 can be passed on to further analysis.

A use wherein said detection device 3 initially is positioned with its needle element 1 pointing upwards may lead to advantages that the transfer and separation of plasma can be done very quickly, preferably within one minute, preferably within 30 seconds, and substantially in one movement and using one hand only. Thus the visual detection may is essentially a "direct" visual detection in the sense that it provides the result almost instantly. However as previously described the invention is not to be limited to such a use. The skilled person understands that it is also possible to apply a detection device 3 onto an upright positioned collection tube, with its sealing member facing upwards.

Figure 3A:
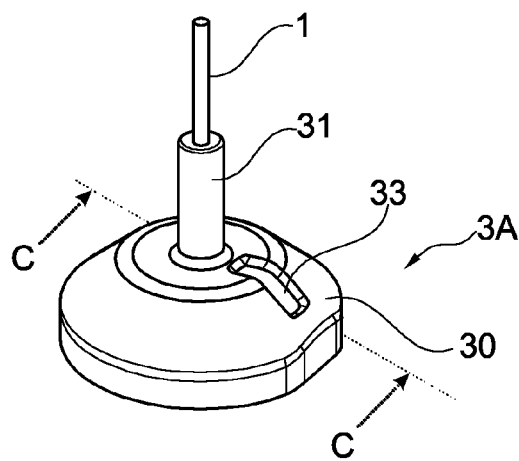
FIGS. 3A-E show different views of a second embodiment of a detection device in accordance with the invention.
Figure 3B:
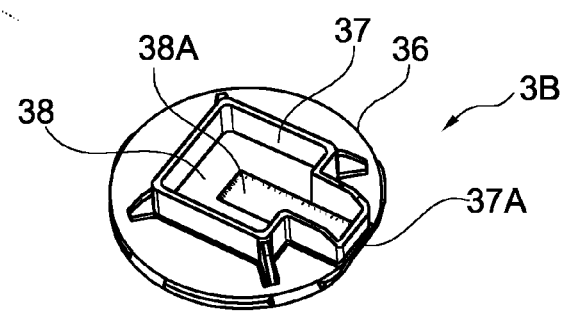
Figure 3C:
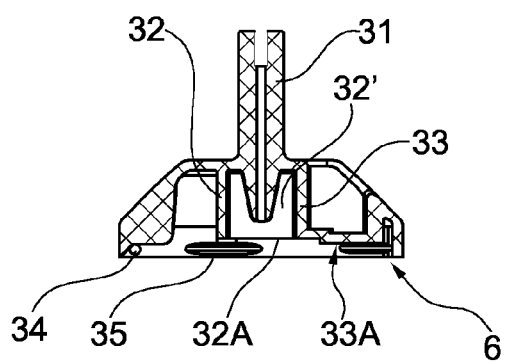
Figure 3D:
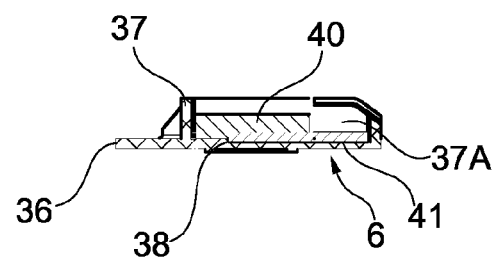
Figure 3E:
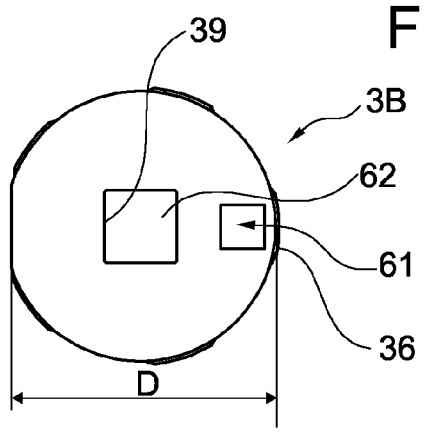

FIGS. 3A to 3E show a further embodiment in accordance with the invention. In general the same kind of parts are used also in this embodiment as have been described in the embodiments above. In FIG. 3A there is shown in a perspective view of the top part where a detection device 3 comprises a top member 3A and a bottom member 3B. At the upper part thereof there is arranged the dispensing body 31 that also fixes the needle 1. At the lower part there is a housing 30. Protruding downwardly from the housing 30, within the interior thereof, there is first pressing member 32 and a second pressing member 33. The first pressing member 32 is in the form of a rectangular protrusion that has a lower end 32A arranged to put pressure on the separation filter 40. Further the first pressing member 32 defines a volume 32' preferably adapted to optimize the collection of an appropriate amount of blood, preferably defining a volume within the range of 50-200 mm$^2$. The maximum cross-sectional width of the first pressing member 32 shall preferably be in the range of 3-10 mm, more preferred 4-7 mm. The second pressing member 33 is preferably arranged with it's lowest end 33A positioned below the lowest end of 32A of the first pressing member 32, in order to put pressure on the detection filter 41, in the area of a detection window 61 (see FIG. 3E). The top part 3A is also arranged with protruding edges 34, preferably arranged with snap in members 35, to facilitate snap in (preferably) fixation of the bottom part 3B. The bottom part 3B is arranged with a peripheral (preferably circular) edge 36 that is adapted to fit into within the edges 34 of the top part 3A. A ridge 37 is arranged protruding on top of the bottom part 3B. The ridge 37 is adapted to encompass a support surface 38 for the two filter members 40, 41. Centrally this ridge 7 basically has the form of a rectangle for containing the separation filter 40. It is evident that also circular members may fulfill the same kind of functionality, or indeed also other forms. The ridge 37 at one side presents an extension 37A, in order to provide space for the detection filter 41. As shown in FIG. 3B the detection filter 41 is smaller than the separation filter 40 and preferably the bottom part 33b is arranged with the a recess 38A especially adapted to the form of the smaller detection filter 41. In FIG. 3E there is a view of the device seen from below, merely presenting the bottom part 3B, also presenting the contours of a kind of non-transparent foil 39 that may be integrated within the bottom part 3B to arrange for first 62 and a second 61 transparent portions, wherein the first portion 62 may be used to visually identify that a sufficient amount blood has been absorbed by the filters 40, 41 and wherein the second window 61 is for the detection.

In FIGS. 4A to 4E there is shown a further embodiment in accordance with the invention, wherein most details are similar to details already presented in connection with FIGS. 3A-3E. Therefore merely distinguishing features will be described in more detail in relation to FIGS. 4A-4E. A significant difference is that the support surface 38 for the filters is arranged with an inclination α. The reason for having the inclination α is that it may improve upon the functionality of the detection device. In some situations there may be a risk that an overfill of blood may occur within the detection device 3. In order to eliminate the risk that such an overfill may cause malfunction, the sloping surface 38 will allow a surplus of blood to flow away from the filter area and pass through an opening 37C within one of the sides of the ridge 37. Further, as in shown if FIG. 4b the bottom part 33B may also be adapted to by means 300 to withhold the surplus to not escape from the device 3, e.g. by means of protruding withholding elements 300, that will hinder blood from escaping from the detection device 3. Moreover, preferably a corresponding opening 32B is arranged within one of the side walls of the first pressing member 32. In a preferred embodiment the inclination α is within the range of 10-30°.

Figure 5:
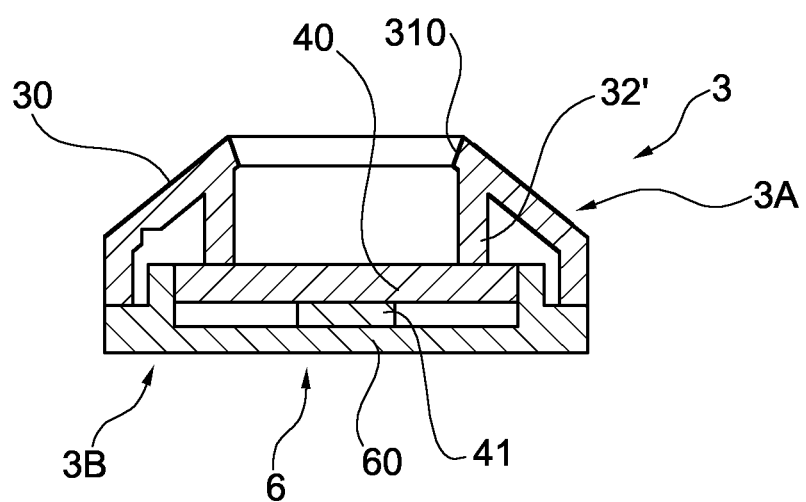
FIG. 5 presents a schematic, cross-sectional view of a forth embodiment in accordance with the invention.

In FIG. 5 there is shown an alternative embodiment of the detection device 3 in accordance with a modified method in accordance within the invention, which device 3 may be used without having the blood sample in any pierceable container, to allow for using some basic advantages of the invention also in connection with other methods for collecting the blood sample. Hence it is foreseen that this embodiment may form the basis of one or more divisional applications focusing on the design of the parts of the device without any needle or dispensing member. According to this embodiment there is also used a top member 3A and a bottom member 3B, but there is no displacing member but a larger opening 300. In this embodiment (without dispensing body) the whole blood may be dispensed on the filter 40 in varying ways. For instance by means of a pipette (not shown), syringe (not shown), or by fixing a retainer means with a capillary acting device (e.g. plastic tube, not shown) within the opening 310. Preferably the opening 310 may adapted to a chosen standard dimension, e.g. the orifice portion of a syringe, etc.

In FIG. 5 the outer periphery of the bottom member 3B corresponds to the outer periphery of the top member 3A. It is evident that also embodiments where the outer periphery of the bottom member 3B is larger than the outer periphery of the top member 3A is fore seen, e.g. by arranging a snap in function wherein the top member fits into the interior of the bottom member 3B.

In the embodiment of FIG. 5 there is also used at least two filters 40, 41 and at least one pressing member 32, to put a pressure on to the filters 40, 41, i.e. to improve the upon the transfer of the plasma through the filters 40, 41, which. shortens the time for the transfer of the plasma to the detection area 39B. (e.g. see 39B in FIG. 3E). Furthermore a ridge 37 is arranged within the bottom part 3B encompassing the space for the filters 40, 41, thereby hindering blood/plasma from escaping (at least at two sides) sideways out of the filters 40, 41. The height of the ridge 37 is preferably in the range 1-4 mm. In some embodiments the whole bottom part 3B may be produce in a transparent material, or partly colored or combined with a foil 39 (see FIG. 3E) in order to present the desired visual portions of the test results.

The detection compartment 6 is generally arranged to contain at least two filters 40, 41, as has been exemplified above. In a preferred embodiment the volume of the detection compartment 6 is within the range of 100-500 ml, more preferred 150-350. As presented in accordance with FIGS. 3A-E and 4A-E the detection compartment 6, can be limited to a certain filter area/volume by means of using a ridge or ridges 37, implying easy adaption of the volume in the compartment to different needs. Furthermore the use of ridges provides the ability to easily apply different forms and any extension of the ridge 37. As further presented in the Figures in a preferred embodiment there is a further limitation within the compartment 6 that presents a limited space, within the ridge 37 of the detection compartment, preferably by using a substantially smaller area for the pressing member 32 and also for the area 38A within the detection compartment 6 that is used for the detection filter 41.

In a preferred embodiment the relation between the total area of the detection compartment 6 and the limited area of the first pressing member 32 is in the range of 10/1 to 2/1. The same relation also applies for the limited area 38A for the detection filter 41 since the area of the detection filter 41 preferably corresponds to (+/−30%) area of the "foot print" of the first pressing member 32. Furthermore also the detection window 61 in the preferred embodiment is smaller than the detection compartment 6. In the preferred embodiment the separation filter 40 has a larger surface area then the detection filter 41. In a preferred embodiment the relation corresponds to what is mentioned above regarding the relation between the detection compartment and the detection filter space.

The skilled person will understand that although a "needle element" conventionally is made of steel material the needle element referred to in this description is not to be limited thereto. In certain circumstances it might suffice with a needle in some other hard material suitable for the specific function, such as hard plastic or glass.

It is foreseen that the invention is not limited to the use of merely two filters 40, 41, but within the scoop of the invention there may be used further filters, e.g. a third filter or fourth (not shown). As a way of example a third filter may be positioned in connection with the second filter 41 to improve readability of the results. For instance such a third filter member (not shown) may contain a substance that will improve upon on the readout, e.g. to achieve a color change. Further, when using three or more filters, the first two filters may be used to mainly achieve the separation and the third one mainly for detection. In the same manner it is foreseen that the first filter may be used alone for mainly achieving separation and the other two for achieving detection.

Further it is within the scope of the invention to use merely one filter body 40, wherein the filter body has a portion thereof treated to function as the detection filter 41 and of course then positioned to at the visualization window 61.

The detection filter 41 may be arranged with chemical means for direct visual detection. Such chemical means for visual detection may lead to a change of color in case hemolysis has occurred whereby it is permitted for safer and more reliable test results and easier evaluation. For instance a common method for colorimetric detection of hemoglobin is Drabkin's reagent, which consists of potassium cyanide. Other alkali cyanides as well as ferricyanides could also be used in such an assay. Further examples of chemical means for visual detection may include colorimetric methods making use of the peroxidase activity of hemoglobin, based on a chromogen such as benzidine compounds with peroxides as substrate. The chemical means (reagents) may be deposited inside the detection compartment 6 either as in dried form or as wet reagent, or as a combination of dry and wet reagents.

The described method for detecting hemolysis using the detection device 3 according to the invention can be performed very easily, quickly and in direct connection to taking a blood sample 12 from a patient. An operator 13 needs only one single hand for performing all the necessary steps for detecting hemolysis, no preparatory steps are required, and the time from applying a test tube 2 on a detection device 3 to readout of the result is extremely short, preferably less than 1 minute, more preferred less than 30 seconds.

Many modifications and other embodiments of the inventions set forth herein will come to mind to one skilled in the art to which these inventions pertain having the benefit of the teachings presented in the foregoing descriptions and the associated figures. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A device for visual detection of hemolysis in a whole blood sample, the device comprising:
   at least one visible detection compartment, including a detection filter that defines a bottom portion of said visible detection compartment,
   a transfer passage connected to said at least one visible detection compartment, said transfer passage arranged to permit transfer of a volume of plasma from said whole blood sample to said at least one visible detection compartment,
   a separation device for separating plasma from blood cells within the whole blood sample before said volume of plasma reaches the at least one visible detection compartment, wherein said at least one visible detection compartment and said separation device are arranged within a housing having a first end and an opposite second end, and wherein said at least one visible detection compartment is positioned at the second end of the housing,
   wherein said transfer passage comprises a needle element held in the housing and having a first end portion for penetrating a sealing member of a pierceable container and a second end portion arranged at said first end of the housing in connection to said separation device, wherein the needle element is integral with the first end of the housing, wherein the needle element is configured for passage of the whole blood sample from the pierceable container to the separation device, and wherein the separation device includes a separation filter adjacent to the second end portion of the needle element so that the whole blood sample upon exiting the second end portion of the needle element will proceed onto the separation filter,
   wherein the housing is configured so that when the device is positioned vertically on a surface the second end of the housing will rest on the surface and the needle element will point in an upward direction, the needle element is configured for passage of the whole blood sample from the pierceable container to the separation device, wherein the separation filter is arranged to collect the whole blood sample and the detection filter is arranged to abut the separation filter, and the separation filter and the detection filter together provide a capillary force to urge the volume of plasma to be transferred from the whole blood sample through the transfer passage to the detection compartment.

2. The device according to claim 1, wherein the pierceable container is a stoppered tube and the first end of the housing comprises a dispensing body including a surface arranged to engage with the stoppered tube.

3. The device according to claim 1, wherein the detection filter is sandwiched between the separation filter and the housing of the device, and wherein the detection filter is visibly arranged inside the at least one visible detection compartment.

4. The device according to claim 1, wherein the separation filter comprises a porous structure providing the capillary action to generate the force urging the volume of plasma to be transferred from the whole blood sample to the at least one visible detection compartment through the transfer passage via the separation device.

5. The device according to claim 1, wherein the detection filter comprises a porous structure providing the capillary action to generate the force urging the volume of plasma to be transferred from the whole blood sample to the at least one visible detection compartment through the transfer passage via the separation device.

6. The device according to claim 1, wherein the second end portion of the needle element is arranged at the first end of the housing adjacent said separation filter.

7. The device according to claim 1, wherein the separation filter has a cross sectional filter area substantially larger than a cross sectional area of said transfer passage.

8. The device according to claim 5, wherein the detection filter is arranged with a chemical reagant for direct visual detection of hemoglobin (Hb).

* * * * *